(12) United States Patent
Ou et al.

(10) Patent No.: US 9,623,074 B2
(45) Date of Patent: Apr. 18, 2017

(54) USE OF IMMUNOMODULATORY PROTEIN IN PROMOTION OF WOUND HEALING OR TREATMENT OF TISSUE INJURY

(71) Applicant: Taipei Medical University, Taipei (TW)

(72) Inventors: Keng-Liang Ou, Taipei (TW); Jungshan Chang, Taipei (TW)

(73) Assignee: 3D GLOBAL BIOTECH INC., Taipei (TW)

( * ) Notice: Subject to any disclaimer, the term of this patent is extended or adjusted under 35 U.S.C. 154(b) by 0 days.

(21) Appl. No.: 13/777,260

(22) Filed: Feb. 26, 2013

(65) Prior Publication Data

US 2014/0079737 A1 Mar. 20, 2014

(30) Foreign Application Priority Data

Sep. 14, 2012 (TW) .............................. 101133908 A (51) Int. Cl.
*A61K 38/16* (2006.01)

(52) U.S. Cl.
CPC .................................... *A61K 38/16* (2013.01)

(58) Field of Classification Search
None
See application file for complete search history.

(56) References Cited

U.S. PATENT DOCUMENTS

| 6,232,341 | B1 | 5/2001 | Chen et al. |
| 7,601,808 | B2 | 10/2009 | Lin |
| 7,888,319 | B2 | 2/2011 | Gourdie et al. |
| 8,084,491 | B2 | 12/2011 | Shapira et al. |
| 8,258,093 | B2 | 9/2012 | Van Dyke |
| 2001/0009915 | A1 | 7/2001 | Lavielle et al. |
| 2011/0318429 | A1* | 12/2011 | Ko .............................. 424/649 |

OTHER PUBLICATIONS

Bowie et al. (Science, 1990, 247:1306-1310).*
Burgess et al. (J. Cell Biol. 111:2129-2138, 1990).*
Lazar et al. (Mol. Cell. Biol., 8:1247-1252, 1988).*
Su et al. (Abstract 3260, Honolulu PRiME 2012, The Electrochemical Society).*
Davidson et al. (http://www.healthline.com/galecontent/ganoderma, published 2005, accessed Dec. 6, 2013).*
Liao et al., "Transcriptionally Mediated Inhibition of Telomerase of Fungal Immunomodulatory Protein From Ganoderma tsugae in A549 Human Lung Adenocarcinoma Cell Line", Mol. Carcinog, 2006, vol. 45, pp. 220-229.

* cited by examiner

*Primary Examiner* — Brian J Gangle
(74) *Attorney, Agent, or Firm* — WPAT, P.C., Intellectual Property Attorneys; Anthony King (57) ABSTRACT

The invention provides a method for promoting wound healing or tissue injury treatment in a subject in need thereof, the method comprising administering to the subject an effective amount of one or more fungal immunomodulatory protein (preferably, *Ganoderma* immunomodulatory protein).

5 Claims, 8 Drawing Sheets

0.04 μg/ml v.s. control    * P < 0.05 .
0.04 μg/ml v.s. 0.2 μg/ml    # p<0.05
0.04 μg/ml v.s. 10 μg/ml    ## p<0.01
0.04 μg/ml v.s. 1 μg/ml, 2 μg/ml    ### p< 0.001
(N=4)

USE OF IMMUNOMODULATORY PROTEIN IN PROMOTION OF WOUND HEALING OR TREATMENT OF TISSUE INJURY

FIELD OF THE INVENTION

The invention relates to a method for promoting wound healing or treating tissue injury. Particularly, the invention uses immunomodulatory protein to promote wound healing or treat tissue injury.

BACKGROUND OF THE INVENTION

Wound healing is a complex dynamic process that results in the restoration of anatomic continuity and function; an ideally healed wound is one that has returned to normal anatomic structure, function and appearance. The classic model of wound healing is divided into three or four sequential, yet overlapping, phases: (1) the immediate response, (2) the inflammatory response, (3) proliferation of wound-edge epithelium and (4) tissue regeneration (remodeling). During the inflammation phase, platelet aggregation and clotting from a matrix which traps the plasma proteins and blood cells to induce the influx of various types of cells. During the cellular proliferation phase, new connective or granulation tissue and blood vessels are formed. During the remodeling phase, granulation tissue is replaced by a network of collagen and elastin fibers leading to the formation of scar tissue.

During human skin wound healing, a critical rate-limiting step is the initiation of the resident epidermal and dermal cells at the wound edge to migrate into the wound bed. The formation of granulation tissue in an open wound allows the reepithelialization phase to take place, as epithelial cells migrate across the new tissue to form a barrier between the wound and the environment. Basal keratinocytes from the wound edges and dermal appendages such as hair follicles, sweat glands and sebacious (oil) glands are the main cells responsible for the epithelialization phase of wound healing. They advance in a sheet across the wound site and proliferate at its edges, ceasing movement when they meet in the middle. Human keratinocytes (HKCs) laterally migrate across the wound bed from the cut edge to eventually close the wound, the process known as re-epithelialization. The dermal cells, including dermal fibroblasts (DFs) and dermal microvascular endothelial cells (HDMECs), start to move into the wound following the HKC migration, where these cells deposit matrix proteins, contract and remodel the newly closed wound and build new blood vessels. Fibroblast cells, located in the dermal layer, play important roles in wound healing by, for example, producing components of the extracellular matrix like collagen and various cytokines, which, in turn, enhance the proliferation and migration of keratinocytes.

A number of composition and methods for wound healing were developed. U.S. Pat. No. 6,232,341 provides a topical pharmaceutical composition for wound healing comprising borneol and bismuth subgallate. U.S. Pat. No. 7,888,319 discloses compositions and methods for promoting wound healing and tissue regeneration, comprising an isolated polypeptide comprising a carboxy-terminal amino acid sequence of an alpha Connexin, or a conservative variant thereof. U.S. Pat. No. 8,084,491 discloses methods of promoting wound healing comprising the administration of a therapeutically effective amount of a composition comprising topiramate. U.S. Pat. No. 8,258,093 provides a pharmaceutical composition comprising a keratin derivative (e.g., keratose, keratine, or a combination thereof).

Lingzhi (a species of *Basidiomycetes*) is an herbal mushroom, used in traditional Chinese medicine for at least 2,000 years. The lingzhi mushroom or reishi mushroom encompasses several fungal species of the genus *Ganoderma*, and most commonly refers to the closely related species, *Ganoderma lucidum* and *Ganoderma tsugae*. Many therapeutic effects have been reported of Lingzhi species, such as immunomodulatory, anti-tumor, hepato-protective, antioxidant, and cholesterol-lowering effects. A new glycoprotein class in Lingzhi named fungal immunomodulatory proteins (FIPs) was recently identified. So far, several FIPs have been isolated and purified, including LZ-8 (from *Ganoderma lucidum*), FIP-fve (from *Flammulina veltipes*), FIP-vvo (from *Volvariella volvacea*), FIP-gts (from *Ganoderma tsugae*), and FIP-gja (from *Ganoderma sinensis*). According to a previous study, FIP-gts from *G. tsugae*, a popular chemopreventive mushroom in Asia, has anti-cancer function and is involved in the regulation of hTERT/telomerase expression (Liao et al., 2006, *Mol Carcinog*, 45, 220-229). US 20100009915 provides a method for suppressing proliferation of a cancer cell and a method for suppressing a tumor cell mobility, comprising providing to the tumor cell a purified polypeptide of a fungal immunomodulatory protein, LZ-8. U.S. Pat. No. 7,601,808 discloses an immunomodulatory protein (GMI) cloned from *Ganoderma microsporum* and this protein has immunomodulator efficiency.

However, none of prior art discloses or suggests the relationship of Lingzhi immunomodulatory protein to wound healing.

SUMMARY OF THE INVENTION

The invention provides a method for promoting healing of a wound or treating a tissue injury in a subject in need thereof, the method comprising administering to the subject an effective amount of one or more fungal immunomodulatory protein immunomodulatory protein or a fragment or variant thereof. Preferably, the fungal immunomodulatory protein is mushroom immunomodulatory protein; more preferably, *Ganoderma* immunomodulatory protein. The embodiments of *Ganoderma* immunomodulatory protein includes LZ-8 (from *G. lucidum*), FIP-gts (from *Ganoderma tsugae*), FIP-gj a (*Ganoderma sinensis*) or the immunomaodulatory protein from *Ganoderma microsporum*.

DETAILED DESCRIPTION OF THE INVENTION

The invention surprisingly found that a fungal immunomodulatory protein (preferably, mushroom immunomodulatory protein; more preferably, *Ganoderma* immunomodulatory protein) significantly can promotes fibroblast cell migration and cell proliferation and accelerate tissue closure. Therefore, the fungal immunomodulatory protein (preferably, mushroom immunomodulatory protein; more preferably, *Ganoderma* immunomodulatory protein) is beneficial to wound healing.

DEFINITIONS

All scientific and technical terms used in this application have meanings commonly used in the art unless otherwise specified. As used in this application, the following words or phrases have the meanings specified.

The terms "a" and "an" refer to one or to more than one (i.e., to at least one) of the grammatical object of the article.

The term "promote," "promotion," and "promoting" refer to an increase in an activity, response, condition, disease, or other biological parameter. The term "promoting wound healing" refers to augmenting, improving, increasing, or inducing closure, healing, or repair of a wound.

The term "subject" includes living organisms such as humans, monkeys, cows, sheep, horses, pigs, cattle, goats, dogs, cats, mice, rats, cultured cells, and transgenic species thereof. In a preferred embodiment, the subject is a human.

The term "administering" includes routes of administration which allow the *Ganoderma* immunomodulatory protein of the invention to perform their intended function.

The term "treat" or "treatment" is meant a method of reducing the effects of a disease or condition. Treatment can also refer to a method of reducing the underlying cause of the disease or condition itself rather than just the symptoms. The treatment can be any reduction from native levels and can be but is not limited to the complete ablation of the disease, condition, or the symptoms of the disease or condition.

The term "effective amount" means an amount of an immunomodulatory protein effective to treat and/or prevent wound healing.

Method for Promoting Wound Healing or Treating Tissue Injury

In one aspect, the invention provides a method for promoting healing of a wound or treating a tissue injury in a subject in need thereof, the method comprising administering to the subject an effective amount of one or more fungal immunomodulatory protein (preferably, mushroom immunomodulatory protein; more preferably, *Ganoderma* immunomodulatory protein) or a fragment or variant thereof.

In one embodiment, the wound healing is promoted or the tissue injury is treated by enhancing progression of wound healing by fibroblast cell migration and proliferation of wound-edge epithelium.

In one embodiment, the wound healing is promoted or the tissue injury is treated by enhancing progression of wound healing by proliferation of wound-edge epithelium In another embodiment, the wound healing is promoted or the tissue injury is treated by accelerating tissue closure.

In another further embodiment, the wound healing is promoted or the tissue injury is treated by not inhibiting neutrophil infiltration.

The term "wound" and "tissue injury" can be used interchangeably. The wound can be an internal wound or an external wound found in any location of a subject. The wounds may include, but are not limited to the following: diabetic wound, diabetic ulcer, mouth ulcer, canker sore, oral lesions, mucous lesion or ulcer, surgical wounds; bites; burns; acid and alkali burns; cold burn (frostbite), sun burn, minor cuts, major cuts, abrasions, lacerations, wounds caused by gunshot or knife injury; wounds caused by congenital disorders; wounds following dental surgery; periodontal disease; wounds following trauma; tumour associated wounds, which can be classified as malignant cutaneous ulcers related to the primary tumour or metastases; ulcers, leg ulcers; foot ulcers; pressure sores and corneal wounds. For example, the method of the invention may be used to treat an injury which causes epidermal damage such as incisions, wounds in which the skin is broken by a cutting instrument, and lacerations, wounds by which the skin is broken by a blunt or dull instrument, and wounds of the skin caused by friction. The method of the invention may also be used to treat dermatological disorders such as burns, Candidiasis and diaper rash, donor and receptor site wounds for skin transplants, ulcers (cutaneous, decubitus, venous stasis, sickle cell, and diabetic), psoriasis, skin rashes, and sunburn photo reactive process, and second and third degree burns. The method of the invention may also be used to protect or accelerate the healing of oral tissue such as mouth sores, burns, surgical sites, and ulcerations. The method of the invention may also be used to treat wounds such as those which result from corneal ulcers, radialkeratotomy, corneal transplants, epikaratophakia and other surgically induced wounds in the eye. In a preferred embodiment, the method of the invention is used to treat wounds such as contusion, incisions and lacerations.

The method of the invention may also be used to treat internal organ wound of a subject. In addition, the method of the invention may also be used to treat oxidative damage during transport and transplantation due to reperfusion injury following ischemia. The method of the invention may be used to abrogate reperfusion injury to such transplant organs as well as resuscitate and cause proliferation of cells.

Tissue injury can result from, for example, a scrape, cut, laceration wound, crush wound, compression wound, stretch injury, bite wound, graze, bullet wound, explosion injury, body piercing, stab wound, burn wound, wind burn, sun burn, chemical burn, surgical wound, surgical intervention, medical intervention, host rejection following cell, tissue or organ grafting, pharmaceutical effect, pharmaceutical side-effect, bed sore, radiation injury, cosmetic skin wound, internal organ injury, disease process (e.g., asthma, cancer), infection, infectious agent, developmental process, maturational process (e.g., acne), genetic abnormality, developmental abnormality, environmental toxin, allergen, scalp injury, facial injury, jaw injury, foot injury, toe injury, finger injury, bone injury, sex organ injury, joint injury, excretory organ injury, eye injury, corneal injury, muscle injury, adipose tissue injury, lung injury, airway injury, hernia, anus injury, piles, ear injury, retinal injury, skin injury, abdominal injury, arm injury, leg injury, athletic injury, back injury, birth injury, premature birth injury, toxic bite, sting, tendon injury, ligament injury, heart injury, heart valve injury, vascular system injury, cartilage injury, lymphatic system injury, craniocerebral trauma, dislocation, esophageal perforation, fistula, nail injury, foreign body, fracture, frostbite, hand injury, heat stress disorder, laceration, neck injury, self mutilation, shock, traumatic soft tissue injury, spinal cord injury, spinal injury, sprain, strain, tendon injury, ligament injury, cartilage injury, thoracic injury, tooth injury, trauma, nervous system injury, aging, aneurism, stroke, digestive tract injury, infarct, or ischemic injury.

Fungal Immunomodulatory Protein

Any immunomodulmory protein from fungal (preferably, mushroom) (such as *Ganoderma, Volvariella* or *Flammulina*) or a functional fragment thereof can be used in the method of the invention. Examples of the immunomodulmory protein include, but is not limited to, LZ-8 or FIP-glu from *Ganoderma lucidum* (Kino, K.; Yamashita, A.; Yamaoka, K.; Watanabe, J.; Tanaka, S.; Ko, K.; Shimizu, K.; Tsunoo, H. Isolation and characterization of a new immunomodulatory protein, lingzhi-8 (LZ-8), from *Ganoderma lucidum*. J. Biol. Chem. 1989, 264, 472-478.), FIP-fve from *Flammulina velutipes* (Ko, J. L.; Hsu, C. I.; Lin, R. H.; Kao, C. L.; Lin, J. Y. A new fungal immunomodulatory protein, FIP-fve isolated from the edible mushroom, *Flammulina velutipes* and its complete amino acid sequence. Eur. J. Biochem. 1995, 228, 244-249), FIP-gts from *G. tsugae* (Lin, W. H.; Hung, C. H.; Hsu, C. I.; Lin, J. Y. Dimerization of the N-terminal amphipathic alpha-helix domain of the fungal immunomodulatory protein from *Ganoderma tsugae* (Fip-gts) defined by a yeast two-hybrid system and site-directed mutagenesis. J. Biol. Chem. 1997, 272, 20044-20048), FIP-vvo from *Volvariella volvacea* (Hsu, H. C.; Hsu, C. I.; Lin, R. H.; Kao, C. L.; Lin, J. Y. Fip-vvo, a new fungal immunomodulmory protein isolated from *Volvariella volvacea*. Biochem. J. 1997, 323, 557-565), FIP-gja from *G. japoncium* (GenBank: AY987805), FIP-gmi from *G. microsporum* (Wu, M. Y.; 20 Hsu, M. F.; Huang, C. S.; Fu, H. Y.; Huang, C. T.; Yang, C. S. A 2.0 structure of GMI, a member of the fungal immunomodulatory protein family from *Ganoderma microsporum*. Protein Crystallogr. 2007, 2, 132), and FIP-gsi from *G. sinense* (Zhou, X. W.; Xie, M. Q.; Hong, F.; Li, Q. Z.; Lin, J. Genomic cloning and characterization of a FIP-gsi gene encoding a fungal immunomodulatory protein from *Ganoderma sinensis* zhao et al (Aphyllophoromycetideae). Int. J. Med. Mushrooms 2009, 11, 77-86). Preferably, the fungal immunomodulmory protein is the *Ganoderma* immunomodulmory protein; more preferably, it is LZ-8 (from *G. lucidum*), FIP-gts (from *Ganoderma tsugae*), FIP-gja (*Ganoderma sinensis*) or the immunomodulmory protein from *Ganoderma microsporum*. The amino acid sequences of these immunomodulmory protein are known in the art (see Appl. Environ. Microbiol. doi:10.1128/AEM.01547-07; GenBank No. B2ZR75. Preferably, the immunomaodulatory protein from *Ganoderma* is LZ-8 or a functional fragment thereof having activity of promoting wound healing or tissue injury treatment. Preferably, the effective amount of said LZ-8 is 1 to 10000 µg/ml. Preferably, the effective amount of said LZ-8 is 500 to 10000 µg/ml.

When specific proteins are referred to herein, variants, derivatives, and fragments are contemplated. Protein variants and derivatives are well understood to those of skill in the art and in can involve amino acid sequence modifications. For example, amino acid sequence modifications typically fall into one or more of three classes: substitutional, insertional or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of one to four residues. Deletions are characterized by the removal of one or more amino acid residues from the protein sequence. These variants ordinarily are prepared by site-specific mutagenesis of nucleotides in the DNA encoding the protein, thereby producing DNA encoding the variant, and thereafter expressing the DNA in recombinant cell culture. Techniques for making substitution mutations at predetermined sites in DNA having a known sequence are well known and include, for example, M13 primer mutagenesis and PCR mutagenesis. Amino acid substitutions are typically of single residues, but can occur at a number of different locations at once; insertions usually will be on the order of about from 1 to 10 amino acid residues. Deletions or insertions preferably are made in adjacent pairs, i.e., a deletion of 2 residues or insertion of 2 residues. Substitutions, deletions, insertions or any combination thereof may be combined to arrive at a final construct. The mutations must not place the sequence out of reading frame and preferably will not create complementary regions that could produce secondary mRNA structure unless such a change in secondary structure of the mRNA is desired. Substitutional variants are those in which at least one residue has been removed and a different residue inserted in its place. For example, the replacement of one amino acid residue with another that is biologically and/or chemically similar is known to those skilled in the art as a conservative substitution. For example, a conservative substitution would be replacing one hydrophobic residue for another, or one polar residue for another. Conservatively substituted variations of each explicitly disclosed sequence are included within the polypeptides provided herein.

Administration of Fungal Immunomodulatory Protein (Preferably, *Ganoderma* Immunomodulatory Protein)

The fungal immunomodulatory protein (preferably, *Ganoderma* immunomodulatory protein) may be formulated as various compositions and administered in a number of ways depending on whether local or systemic treatment is desired, and on the area to be treated. Administration may be topically (including ophthalmically, vaginally, rectally, intranasally), orally, by inhalation, or parenterally, for example by intravenous drip, subcutaneous, intraperitoneal or intramuscular injection.

Compositions for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Compositions for topical administration may include ointments, lotions, creams, gels (e.g., poloxamer gel), drops, suppositories, sprays, liquids and powders. Conventional pharmaceutical carriers, aqueous, powder or oily bases, thickeners and the like may be necessary or desirable. The disclosed compositions can be administered, for example, in a microfiber, polymer (e.g., collagen), nanosphere, aerosol, lotion, cream, fabric, plastic, tissue engineered scaffold, matrix material, tablet, implanted container, powder, oil, resin, wound dressing, bead, microbead, slow release bead, capsule, injectables, intravenous drips, pump device, silicone implants, or any bio-engineered materials.

Compositions for oral administration include powders or granules, suspensions or solutions in water or non-aqueous media, capsules, sachets, or tablets. Thickeners, flavorings, diluents, emulsifiers, dispersing aids or binders may be desirable.

The exact amount of the fungal immunomodulatory protein (preferably, *Ganoderma* immunomodulatory protein) required will vary from subject to subject, depending on the species, age, weight and general condition of the subject, the severity of the allergic disorder being treated, the particular nucleic acid or vector used, its mode of administration and the like. An appropriate amount can be determined by one of ordinary skill in the art using only routine experimentation given the teachings herein.

For example, the fungal immunomodulatory protein (preferably, *Ganoderma* immunomodulatory protein) may be used in topical compositions, ingestible comporsitions, and tissue culture medium to protect mammalian cells and increase the resuscitation rate of mammalian cells and enhance cell reproduction. For example, the fungal immunomodulatory protein (preferably, *Ganoderma* immunomodulatory protein) may be used in topical skin care compositions to protect and increase the resuscitation rate of skin tissues such as in the treatment of various dermatological disorders such as photo-aging and sunburn photo-reactive processes. Injury of skin can occur for a variety of reasons. Injury often occurs to individuals who wash their hands often, to individuals who are exposed to stressful environmental conditions (overexposure to sunlight or chemical) or to the elderly or individuals with an underlying disease.

For example, the fungal immunomodulatory protein (preferably, *Ganoderma* immunomodulatory protein) may also be used in the form of a mouth wash or a spray to protect and accelerate the healing of injured oral tissue such as mouth sores and burns. The fungal immunomodulatory protein (preferably, *Ganoderma* immunomodulatory protein) may further be used in opthalmological preparations such as eye care products to neutralize hydrogen peroxide used in the cleaning of contact lenses. The fungal immunomodulatory protein (preferably, *Ganoderma* immunomodulatory protein) may also be used in anorectal creams and suppositories to treat such conditions as pruritus ani, procitis, anal fissures, and hemorrhoids. The wound healing compositions may also be used in ingestible compositions and increase the resuscitation rate of erosions, stomach ulcers, and hemorrhages in the gastric mucosa. Other injestible therapeutic compositions include: stroke medications; autoimmune disease medications; arthritis medications; ulcer medications; cancer medications (cytotoxic agents); heart medications to improve regional ventricular function and restore normal heart rate and pressure functions; lung medications to repair injured tissues; liver medication to suppress lipogenesis of alcoholic origin and prevent hepatic steatosis; kidney medication to suppress urinary calculi; detoxification medication to antagonize heavy metal poisoning, cyanide poisoning, sodium sulfide poisoning, other types of poisoning; and reduce and neutralize the production of oxygen radicals which produces tissue injury, to protect and further enhance the resuscitation rate of the injured mammalian cells. The fungal immunomodulatory protein (preferably, *Ganoderma* immunomodulatory protein) may be used in injestible products to treat inflammatory diseases such as hepatitis, gastritis, colitis, esophagitis, arthritis, and pancreatitis.

The fungal immunomodulatory protein (preferably, *Ganoderma* immunomodulatory protein) of the present invention may also be used in tissue culture media and organ transplant media to reduce and prevent injury to mammalian cells and increase the resuscitation rate of injured mammalian cells. The fungal immunomodulatory protein (preferably, *Ganoderma* immunomodulatory protein) may be useful to abrogate reperfusion injury to such transplant organs as well as resuscitate and cause proliferation of cells.

The fungal immunomodulatory protein (preferably, *Ganoderma* immunomodulatory protein) can be administrated further in combination with any known or newly discovered substance that can be administered to a wound, tissue injury, site of inflammation or cancer. For example, the provided composition can further comprise one or more of classes of antibiotics (e.g. Aminoglycosides, Cephalosporins, Chloramphenicol, Clindamycin, Erythromycins, Fluoroquinolones, Macrolides, Azolides, Metronidazole, Penicillin's, Tetracycline's, Trimethoprim-sulfamethoxazole, Vancomycin), steroids (e.g. Andranes (e.g. Testosterone), Cholestanes (e.g. Cholesterol), Cholic acids (e.g. Cholic acid), Corticosteroids (e.g. Dexamethasone), Estraenes (e.g. Estradiol), Pregnanes (e.g. Progesterone), narcotic and non-narcotic analgesics (e.g. Morphine, Codeine, Heroin, Hydromorphone, Levorphanol, Meperidine, Methadone, Oxydone, Propoxyphene, Fentanyl, Methadone, Naloxone, Buprenorphine, Butorphanol, Nalbuphine, Pentazocine), chemotherapy (e.g. anti-cancer drugs such as but not limited to Altretamine, Asparaginase, Bleomycin, Busulfan, Carboplatin, Carmustine, Chlorambucil, Cisplatin, Cladribine, Cyclophosphamide, Cytarabine, Dacarbazine, Diethylstilbesterol, Ethinyl estradiol, Etoposide, Floxuridine, Hudarabine, Fluorouracil, Flutamide, Goserelin, Hydroxyurea, Idarubicin, Ifosfamide, Leuprolide, Levamisole, Lomustine, Mechlorethamine, Medroxyprogesterone, Megestrol, Melphalan, Mercaptopurine, Methotrexate, Mitomycin, Mitotane, Mitoxantrone, Paclitaxel, pentastatin, Pipobroman, Plicamycin, Prednisone, Procarbazine, Streptozocin, Tamoxifen, Teniposide, Vinblastine, Vincristine), anti-inflammatory agents (e.g. Alclofenac; Alclometasone Dipropionate; Algestone Acetonide; alpha Amylase; Amcinafal; Amcinafide; Amfenac Sodium; Amiprilose Hydrochloride; Anakinra; Anirolac; Anitrazafen; Apazone; Balsalazide Disodium; Bendazac; Benoxaprofen; Benzydamine Hydrochloride; Bromelains; Broperamole; Budesonide; Carprofen; Cicloprofen; Cintazone; Cliprofen; Clobetasol Propionate; Clobetasone Butyrate; Clopirac; Cloticasone Propionate; Cormethasone Acetate; Cortodoxone; Decanoate; Deflazacort; Delatestryl; Depo-Testosterone; Desonide; Desoximetasone; Dexamethasone Dipropionate; Diclofenac Potassium; Diclofenac Sodium; Diflorasone Diacetate; Diflumidone Sodium; Diflunisal; Difluprednate; Diftalone; Dimethyl Sulfoxide; Drocinonide; Endrysone; Enlimomab; Enolicam Sodium; Epirizole; Etodolac; Etofenamate; Felbinac; Fenamole; Fenbufen; Fenclofenac; Fenclorac; Fendosal; Fenpipalone; Fentiazac; Flazalone; Fluazacort; Flufenamic Acid; Flumizole; Flunisolide Acetate; Flunixin; Flunixin Meglumine; Fluocortin Butyl; Fluorometholone Acetate; Fluquazone; Flurbiprofen; Fluretofen; Fluticasone Propionate; Furaprofen; Furobufen; Halcinonide; Halobetasol Propionate; Halopredone Acetate; Ibufenac; Ibuprofen; Ibuprofen Aluminum; Ibuprofen Piconol; Ilonidap; Indomethacin; Indomethacin Sodium; Indoprofen; Indoxole; Intrazole; Isoflupredone Acetate; Isoxepac; Isoxicam; Ketoprofen; Lofemizole Hydrochloride; Lomoxicam; Loteprednol Etabonate; Meclofenamate Sodium; Meclofenamic Acid; Meclorisone Dibutyrate; Mefenamic Acid; Mesalamine; Meseclazone; Mesterolone; Methandrostenolone; Methenolone; Methenolone Acetate; Methylprednisolone Suleptanate; Morniflumate; Nabumetone; Nandrolone; Naproxen; Naproxen Sodium; Naproxol; Nimazone; Olsalazine Sodium; Orgotein; Orpanoxin; Oxandrolane; Oxaprozin; Oxyphenbutazone; Oxymetholone; Paranyline Hydrochloride; Pentosan Polysulfate Sodium; Phenbutazone Sodium Glycerate; Pirfenidone; Piroxicam; Piroxicam Cinnamate; Piroxicam Olamine; Pirprofen; Prednazate; Prifelone; Prodolic Acid; Proquazone; Proxazole; Proxazole Citrate; Rimexolone; Romazarit; Salcolex; Salnacedin; Salsalate; Sanguinarium Chloride; Seclazone; Sermetacin; Stanozolol; Sudoxicam; Sulindac; Suprofen; Talmetacin; Talniflumate; Talosalate; Tebufelone; Tenidap; Tenidap Sodium; Tenoxicam; Tesicam; Tesimide; Testosterone; Testosterone Blends; Tetrydamine; Tiopinac; Tixocortol Pivalate; Tolmetin; Tolmetin Sodium; Triclonide; Triflumidate; Zidometacin; Zomepirac Sodium), or anti-histaminic agents (e.g. Ethanolamines (like diphenhydrmine carbinoxamine), Ethylenediamine (like tripelennamine pyrilamine), Alkylamine (like chlorpheniramine, dexchlorpheniramine, brompheniramine, triprolidine), other anti-histamines like astemizole, loratadine, fexofenadine, Bropheniramine, Clemastine, Acetaminophen, Pseudoephedrine, Triprolidine).

EXAMPLE

Example 1

Progression of Wound Healing Followed by Skin Wounds in Dorsal Region of Mice

Animals 8-12 weeks C57BL/6 male mice were anesthetized with induction of isoflurane inhalation and maintained with intraperitoneal injection of urethane (1 g/kg). Four full-thickness wounds were generated on each side of the midline with a sterile disposable biopsy punch. Each wound was photographed daily by zoom stereo microscope for seven days Animals were sacrificed at day 7 and the wounds with surrounded area were removed and fixed in solution containing 4% formaldehyde for histological analysis.
Administration of LZ-8

LZ-8 was provided by Yeastern Biotech Co., Ltd., Taiwan. LZ-8 was dissolved in phosphate buffered saline (PBS) and stored at 4° C. until used. Ten microliters phosphate buffered saline (PBS) containing various concentrations of LZ-8 kindly provided by Yeastern Biotech Co., Ltd. were applied daily into midline dorsal skin wounds.
Wound Healing Assay The human lung fibroblast WI-38 cell was seeded and grown MEM medium in 6-well plates. Cells were scratched and removed using 1 ml sterile blue pipette tips when the cells grew up to 90% confluence. The artificially injury-gapped monolayer was created with the identical width for further studies. Furthermore, cells were cultured under different concentrations of LZ-8 and the recovery from gapping injury was reordered and measured. The images of injured monolayer were captured by a combined 40× objective and 10× ocular lens on Leica microscope.

Figure 1:
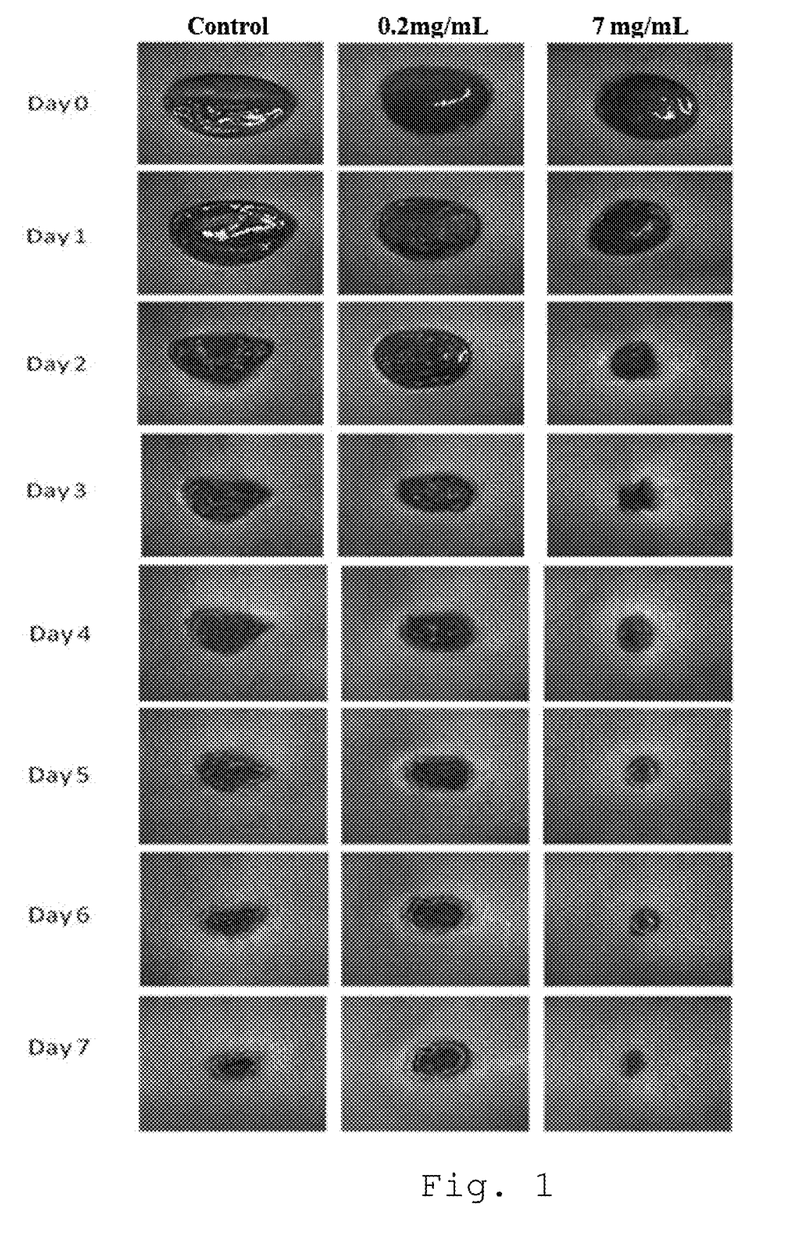
FIG. 1 shows the skin wounds in dorsal region of C57BL/6 mice which were treated with LZ-8 daily and were imaged at day 0, 1, 2, 3, 4, 5, 6, 7. The progression of wound healing was photographed at the same distance over seven days.
Figure 2:
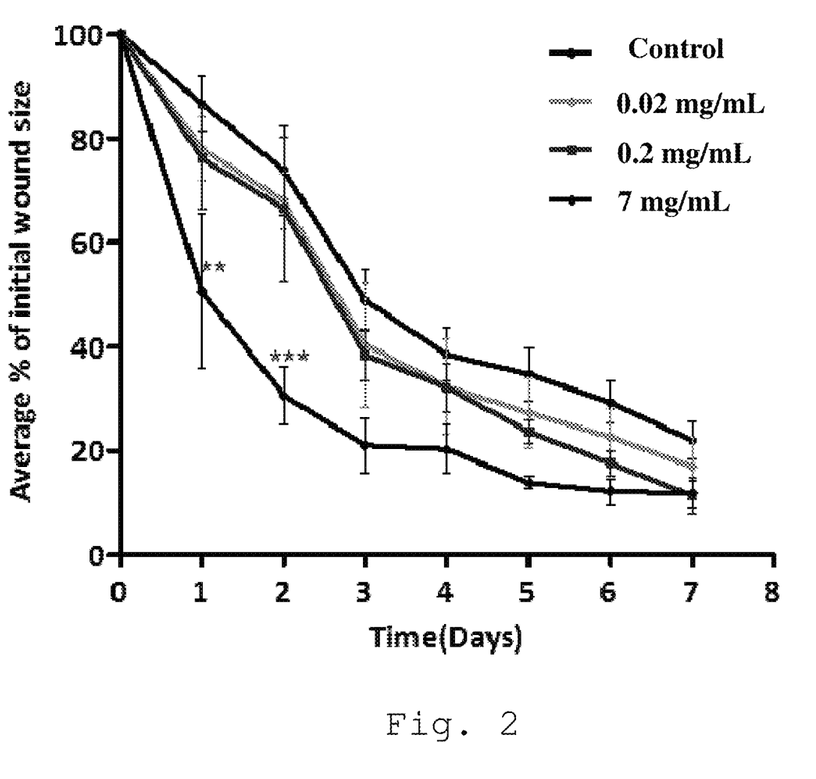
FIG. 2 is the fraction of initial wound size plotted versus time. (three animals per group)  $P<0.001$.* $P<0.0005$.
Figure 3:
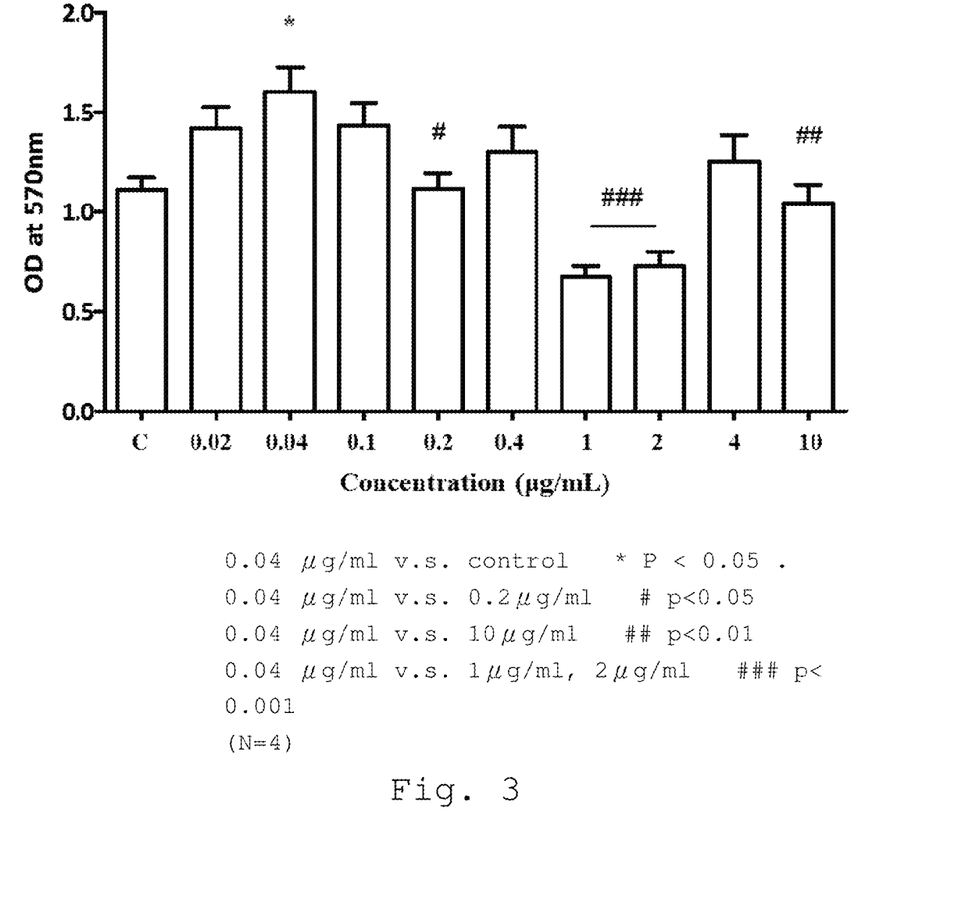
FIG. 3 is the cell proliferation measurement using MTT assay. LZ-8s at various concentrations of were used to treat the human lung fibroblast WI-38 and detected after 24 hrs. 2 μg/ml vs. control * $P<0.05$ 0.2 μg/ml vs. 10 μg/ml# $p<0.05$ 2 μg/ml vs. 50 μg/ml, 100 μg/ml## $p<0.001$.
Figure 4:
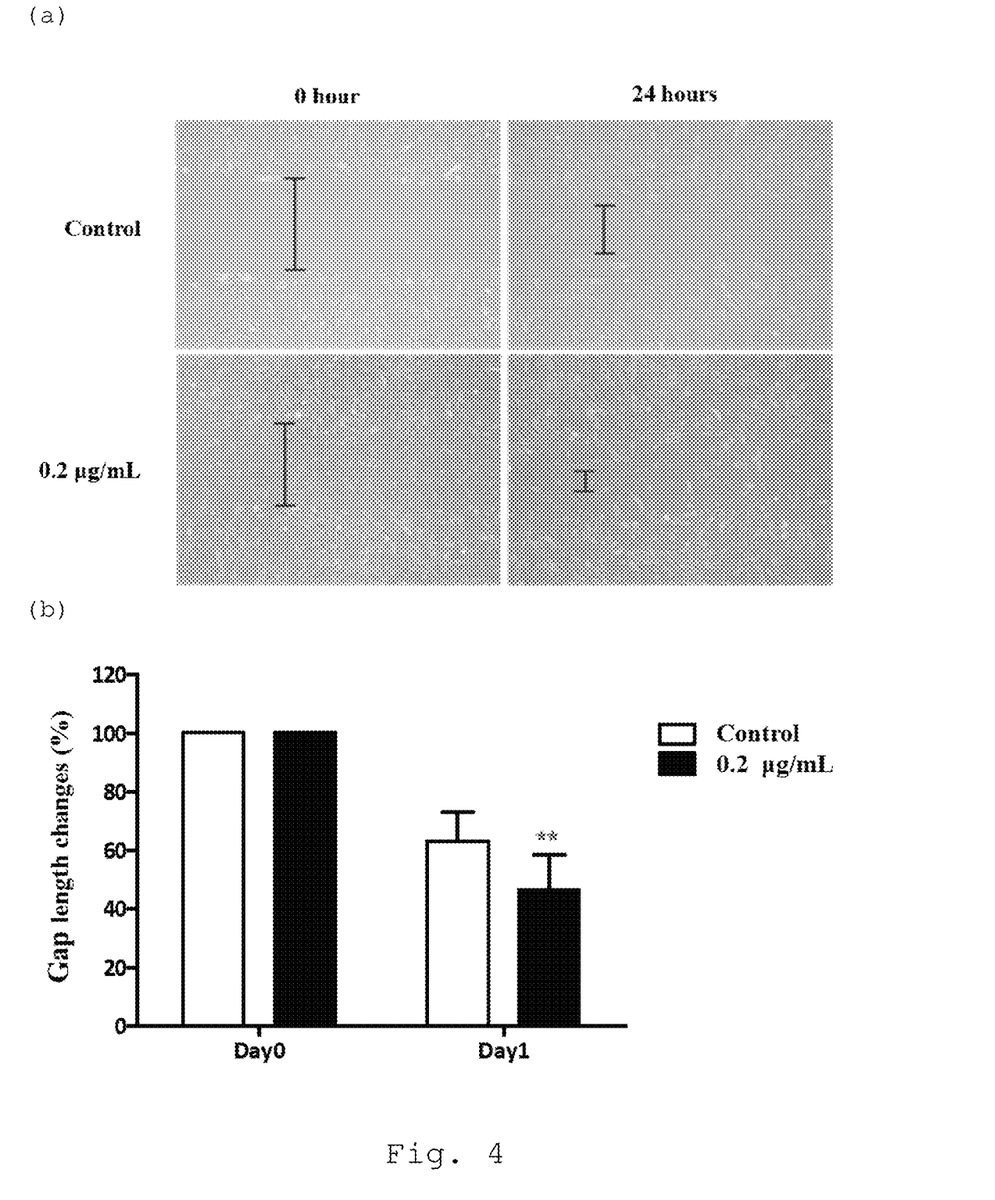
FIG. 4 shows the wound healing assay performed by the human lung fibroblast WI-38 migration. (a) Cells were immersed in 10 μg/ml LZ-8 and photographed after 24 hrs. (b) The cell migration length of the control group was plotted versus time (each group repeated five times).** $P<0.001$.

The result showed that mice with administration of LZ-8 had a better recovery from injury underlying the smaller size of wounds compared to control mice and the tissue repair rate displayed a dosage-dependent trend. Mice with 0.2 mg/ml administration exhibited the smallest wound remaining at day 7, suggesting LZ-8 can accelerate tissue repair and healing in our experimental animals (FIG. 1). The wound area was measured and quantified. 90% of initial wounds recovered in mice treated with 0.2 mg/ml LZ-8, which was greater than other mice (treated with 0.01 and 0.02 mg/ml LZ-8) does. It suggests LZ-8 is a qualified candidate for wound healing therapeutics and 0.2 mg/ml is an optimal dosage in our animal model (FIG. 2). The human lung fibroblast WI-38 cultured in MEM medium containing 0.04 µg/ml of LZ-8 showed better proliferation rate and survival compared to others (FIG. 3). In the in vitro wound healing assay, cells with treatment of 0.2 µg/ml of LZ-8 demonstrated the smallest gap (60% recovery) with 20% enhancement comparing to cells without any treatment in 24 hours (FIG. 4a, 4b).

Example 2

Progression of Wound Healing Followed by Liver Injury in Dorsal Region of Mice

LZ-8 was provided by Yeastern Biotech Co., Ltd., Taiwan. LZ-8 was dissolved in phosphate buffered saline (PBS) and stored at 4° C. until used.
Animals & Surgical Device Sixteen healthy male Sprague-Dawley rats, weighing 200 to 300 g, procured from BioLASCO (Taiwan) were used for the experiments. The animals were maintained (in accordance with the guidelines for the care and use of laboratory animals) at 25° C. and exposed to 12 h of dark and 12 h of light. They were fed with standard balanced pellet diet and water ad libitum. The protocols for animal experiments were reviewed and approved by the Institutional Animal Care and Use Committee for Taipei Medical University (LAC-99-0037). Rats were marked to permit individual identification and were kept in their cages for 14 days prior to experimentation to allow for acclimatization to the laboratory conditions. No reusable commercial electrosurgical monopolar tip (ERBE, No. 20191-377, USA; needle type, stainless steel 304) was used.
Surgical Procedure General anesthesia was induced with inhaled isoflurane of the animals. The operative site was cleansed and draped in a sterile fashion. Conventional stainless steel (SS) needle electrodes were used with an electrosurgical unit. The liver was exposed through midline laparotomy with a retractor to avoid injury to the liver. An unmodified SS-needle was inserted to the liver lobe (4 mm in depth) to create an anterior lesion, using a fixed power setting (60 W) with a fixed activation time (4 seconds). The power setting and activation time were commonly used parameters and were based on settings from a previous study. For LZ-8 protein group, 10 µl of 1 mg/ml LZ-8 protein solution will drop on the wound surface by pipetment immediately; and for control group, as same as experiment group, 10 µl of normal saline will drop on the wound surface by pipetment immediately.

Histological Examination to Detect the Injury Area

Animals were sacrificed on days 0, 3, 7, and 28 post-operation, respectively. The livers were removed and fixed in 10% formalin of neutral buffer. The samples were then dehydrated in a graded series of ethanol and embedded in paraffin wax. Consecutive sections were cut from the paraffin blocks into 5 µm slide and deparaffinized. The sections were stained with Hematoxylin and Eosin (H&E, 3008-1 &3204-2, Muto, Japan). The total injury area caused by the SS-needle was measured by using image analysis software (SPOT basic software, SPOT imaging solutions, MI, USA). In addition, different histological features were observed in the injury site. Therefore, the injury area was further divided into different classifications to demonstrate the injury caused by thermal spread, and the area of every portion was measured.

Figure 5:
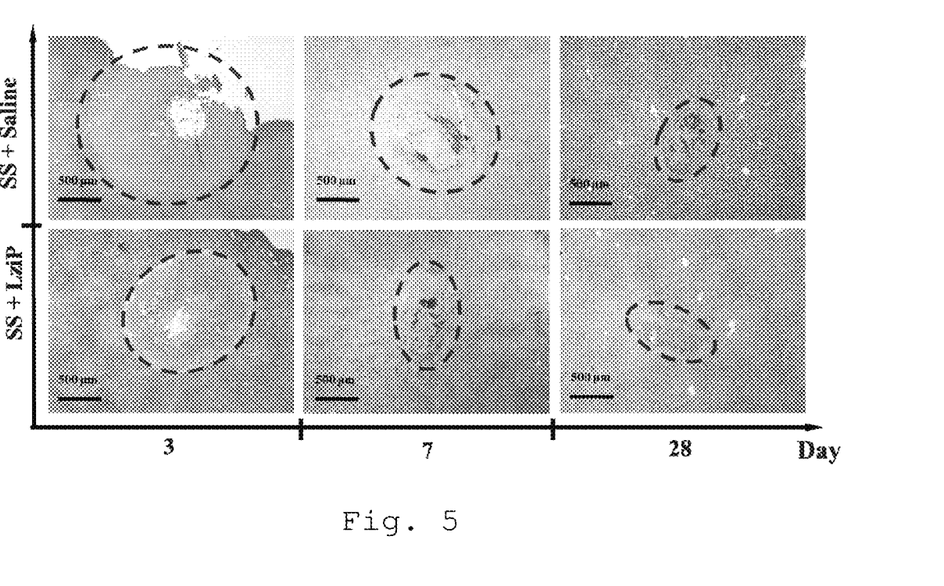
FIG. 5 shows the electrosurgical wound area of LZ-8 treatment group and saline group which were histological-photographed after 3, 7 and 28 days, wherein the dotted line shows the injury area, wherein the SS means stainless steel electrosurgical device and wherein the LZiP means LZ-8.
Figure 6:
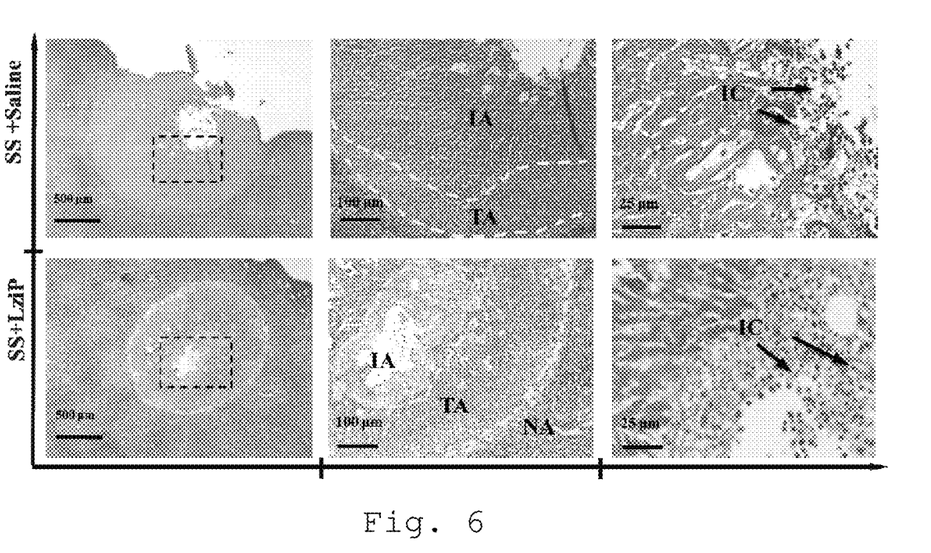
FIG. 6 shows the histology photographs of electrosurgical wound area of LZ-8 treatment group and saline group which were photographed after 3 days, wherein the SS means stainless steel electrosurgical device, LZiP means LZ-8, NA means normal area, FA means fibrosis area and NE means necrosis area.
Figure 7:
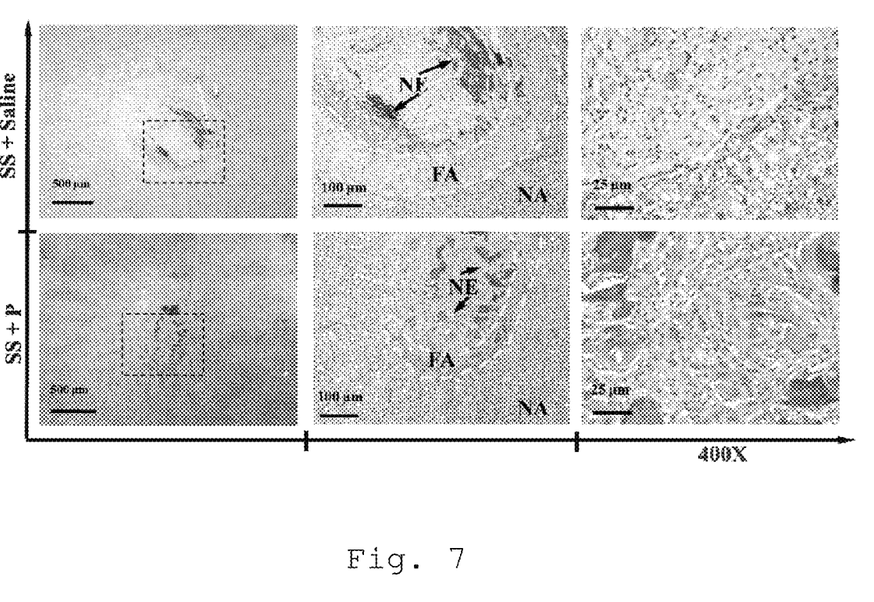
FIG. 7 shows the histology photographs of electrosurgical wound area of LZ-8 treatment group and saline group which were photographed after 7 days, wherein the SS means stainless steel electrosurgical device, LZiP means LZ-8, NA means normal area, FA means fibrosis area and NE means necrosis area, and wherein the arrow points out the necrosis area.
Figure 8:
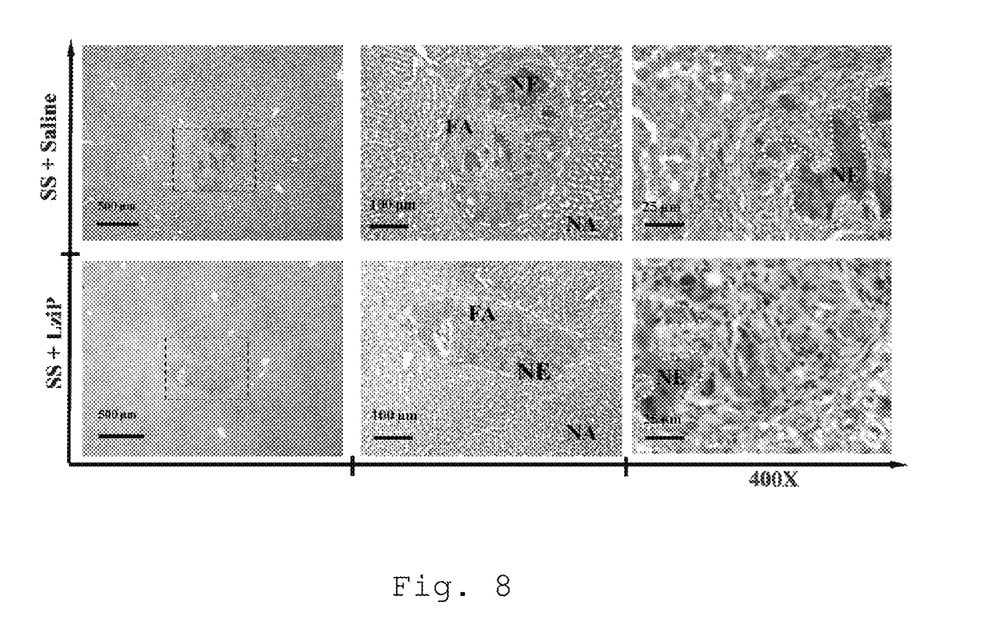
FIG. 8 shows the histology photographs of electrosurgical wound area of LZ-8 treatment group and saline group which were photographed after 28 days, wherein the SS means stainless steel electrosurgical device, LZiP means LZ-8, NA means normal area, FA means fibrosis area and NE means necrosis area.

The effect of LZ-8 on tissue injury healing of electrosurgical wound was analyzed by histology. The result also showed that electrosurgical wound with administration of LZ-8 had a better recovery from injury compared to control group animals. After 3 days treatment, the electrosurgical wound area of LZ-8 treatment group animal was found to be smaller than that of the saline group (FIG. 5). The wound healing speed of the LZ-8 treatment group was also found to be faster than the saline group. FIG. 6 shows the immune cell immersion region of the electrosurgical wound. The immune cell immersion could be observed in both treatment groups on day 3. After 7 days, the necrosis or fibrosis region could be observed in the electrosurgical wound. FIG. 7 shows that the necrosis or fibrosis region of the LZ-8 treatment group was smaller than saline group. Furthermore, on day 28, the electrosurgical wound of the LZ-8 treatment group was almost healed, with only a small area of fibrosis or necrosis region (FIG. 8). In contrast, the saline group still had a visible electrosurgical wound and large area of fibrosis and necrosis region.

What is claimed is:

1. A method for promoting healing of a surgically induced wound or treating a tissue injury in a subject in need thereof, the method comprising administering to the subject a composition comprising a fungal immunomodulatory protein LZ-8 which is isolated from *Ganoderma lucidum*, wherein the LZ-8 is present in the concentration of 10 to 10000 µg/ml and wherein the surgically induced wound or tissue injury is internal organ wound or traumatic soft tissue injury.

2. The method of claim 1, wherein the subject is human, monkey, cow, sheep, horse, pig, cattle, goat, dog, cat, mouse, rat, or transgenic species.

3. The method of claim 1, wherein the organ is liver or bone.

4. A method for treating wounds in the eye in a subject in need thereof, the method comprising administering to the subject a composition comprising a fungal immunomodulatory protein LZ-8 which is isolated from *Ganoderma lucidum*, wherein the LZ-8 is present in the concentration of 10 to 10000 µg/ml.

5. The method of claim 1, wherein the soft tissue is cartilage.

* * * * *